United States Patent [19]
Hubbard

[11] Patent Number: 5,356,371
[45] Date of Patent: Oct. 18, 1994

[54] SHAPEABLE THUMB SUPPORT

[75] Inventor: Craig J. Hubbard, Port Macquarie, Australia

[73] Assignee: Wildtman Australia Pty. Limited, Port Macquarie, Australia

[21] Appl. No.: 27,196

[22] Filed: Mar. 5, 1993

[51] Int. Cl.⁵ ............................................. A61F 5/04
[52] U.S. Cl. ..................... 602/22; 602/21; 602/6; 602/5; 2/21
[58] Field of Search ............. 602/21, 22, 2, 6, 64; 462/44; 273/188 R, 189 R, 189 A; 2/16, 21

[56] References Cited

U.S. PATENT DOCUMENTS

| | | | |
|---|---|---|---|
| 1,471,948 | 10/1923 | Cox et al. | 602/22 |
| 2,523,606 | 9/1950 | Young | 602/22 X |
| 3,533,407 | 10/1970 | Smith | 273/189 A |
| 4,138,108 | 2/1979 | Robinson | 273/189 A X |
| 4,732,142 | 3/1988 | Hurlburt et al. | 602/22 X |
| 4,862,877 | 9/1989 | Barber | 602/22 |
| 5,101,812 | 4/1992 | Wang | 602/22 |
| 5,147,285 | 9/1992 | Buxton | 602/22 |
| 5,168,577 | 12/1992 | Detty | 2/16 |

FOREIGN PATENT DOCUMENTS

| | | | |
|---|---|---|---|
| 2588183 | 4/1987 | France | 602/22 |
| 2650175 | 2/1991 | France | 602/21 |
| 2650176 | 2/1991 | France | 602/21 |

Primary Examiner—Richard J. Apley
Assistant Examiner—Beverly A. Meindl
Attorney, Agent, or Firm—Chase & Yakimo

[57] ABSTRACT

A thumb support is provided which both guides and limits thumb movement from the back of the hand while leaving the palm surfaces unobstructed for use. The support contains a moldable support member which can be shaped to conform to the back and sides of the thumb of the user.

13 Claims, 2 Drawing Sheets

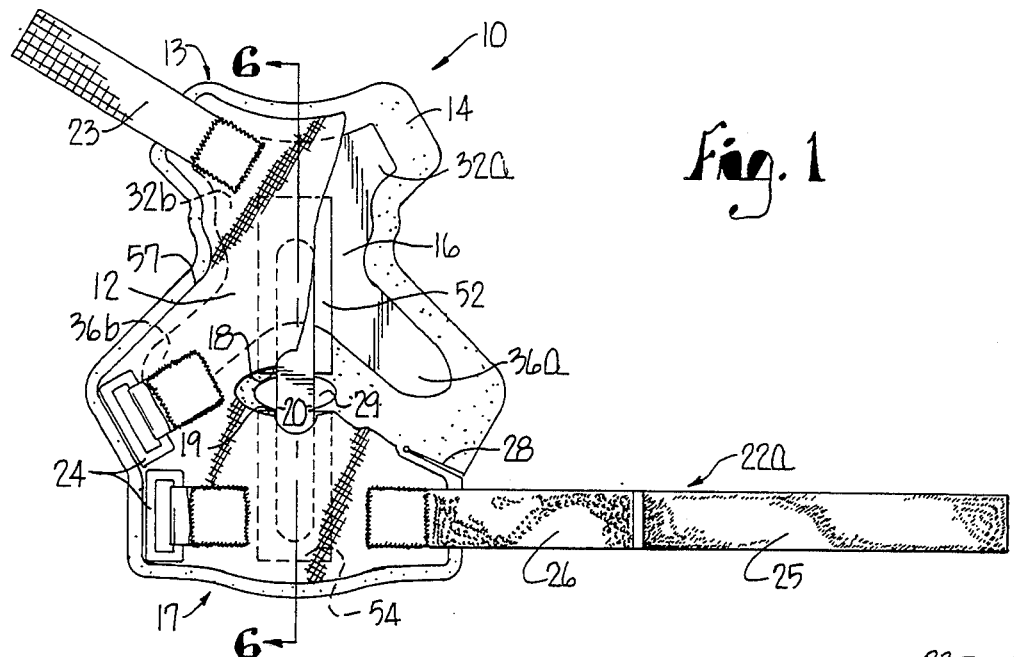
Fig. 1
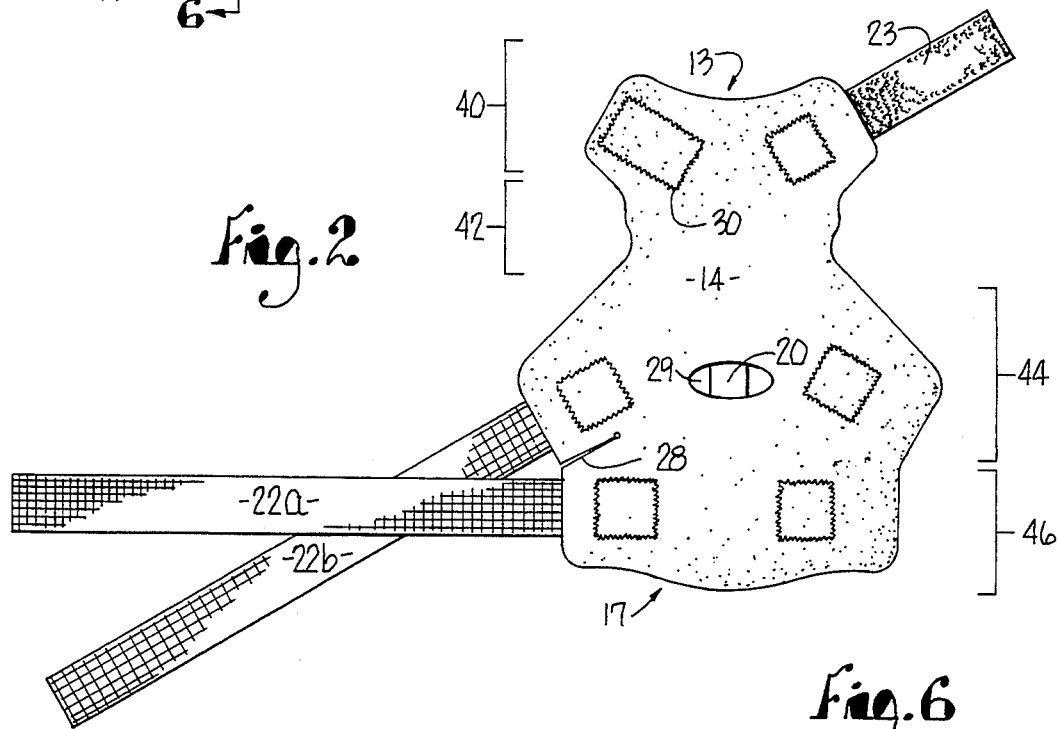
Fig. 2
Fig. 6
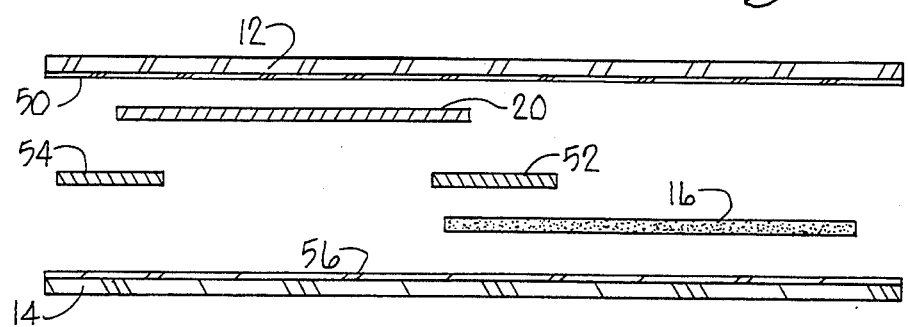

SHAPEABLE THUMB SUPPORT

BACKGROUND OF THE INVENTION

The present invention relates to hand and thumb supports worn for protection and/or rehabilitation, and in particular to a moldable thumb brace which provides functional support to the thumb without obstructing the palm and impairing the ability to grasp an object by the hand.

Hand splints and similar devices for the fingers and thumb typically utilize a rigid splint which fixes the thumb or other body part in a single position and prevents any flexing or hyperextension of the splinted or supported appendage. Such rigid or fixed methods of support are modeled upon the rigid splints utilized in the setting of bone fractures, the object in setting bone fractures being complete immobilization of the limb to enable correctly aligned healing of the fracture. Such complete immobilization also is intended to protect the fractured limb and discourage its use during the healing process.

However, it is often desirable to support a sprained or strained or otherwise injured appendage, such as a finger or thumb, in a manner which does not completely immobilize the digit and which permits near normal, but guided and restrained use of the digit. Prior art devices generally do not permit such restricted and guided movement of the injured digit, but rather tend to fix the digit in a single immobilized position typical of a fractured finger or thumb splint. Furthermore, prior art supports or splints are generally of designs which obstruct the palm of the hand and the grasping surfaces of the fingers and thumb thus rendering the grasping ability substantially debilitated.

Additionally, a problem presented is that prior splints or supports are typically constructed in a generalized configuration and cannot be closely adapted to the individual size and shape of the digit to be supported. Another limitation is that flexing of the thumb or other digit of the hand is determined by the materials used and their inherent rigidity. No provision is made for the adaption of the splint or support to the abilities of the particular individual or the limitations of the particular injuries.

Therefore, it is an object of the present invention to provide a support for a thumb or other digit of the hand which permits movement of the digit in a reduced, but supported range of motion and which does not immobilize the digit.

Another object of the present invention is to provide a device for supporting and guiding movement of a thumb or other digit which does not obstruct the palm surfaces of the hand or the digits, but allows relatively unimpaired grasping of articles by the hand.

Yet another object of the present invention is to provide a support for a digit which is moldable to conform to the shape of the digit in order to guide movement in a defined direction.

Yet another object of the present invention is to provide a support for a hand digit which can be repetitively molded to conform to changes in hand dimensions or to be utilized by a second user.

Other objects and advantages of this invention will become apparent from the following description taken in connection with the accompanying drawings, wherein is set forth by way of illustration and example, an embodiment of this invention.

SUMMARY OF THE INVENTION

In accordance with the principles of the present invention, a thumb support or brace is disclosed having a cushioned base layer for application to the back of the hand and to which is attached a flat, relatively thin, moldable digit support member that may be warmed and shaped in order to conform the support member to the general shape of the thumb. A splint is provided which aligns, generally, along the dorsal surface of the thumb and which is received in a pocket to allow movement and removal of the splint as well as the accommodation of splints of varying length and rigidity. The foregoing layers are covered by an outer flexible material which protects the individual layers and provides a strong surface for attachment of fasteners, such as VELCRO ® tabs, which may be utilized to apply the support or brace about the wrist, hand and thumb.

An inventive method for supporting the back and sides of a hand digit is also provided which comprises the steps of warming a flat, relatively thin support member until it is pliable, applying the pliable support member to the back of the hand and digit to be supported, molding the member about the digit and cooling the support member while in the molded shape or configuration, and then fastening the molded support member about the hand and supported digit.

DESCRIPTION OF THE DRAWINGS

FIG. 1 is a top plan view of the device with a portion of the outer flexible layer broken away to reveal the moldable support member, splint receiving means and splint;

FIG. 2 is a bottom plan view of the device showing the cushion layer and attachment points of fasteners for securing the device to the hand and thumb;

FIG. 6 is an exploded, enlarged cross-sectional view taken along line 6—6 of FIG. 1 and showing the moldable support member, the splint, and the splint receiving means sandwiched between the base cushion layer and the outer flexible layer.

DESCRIPTION OF THE PREFERRED EMBODIMENT

Figure 3:
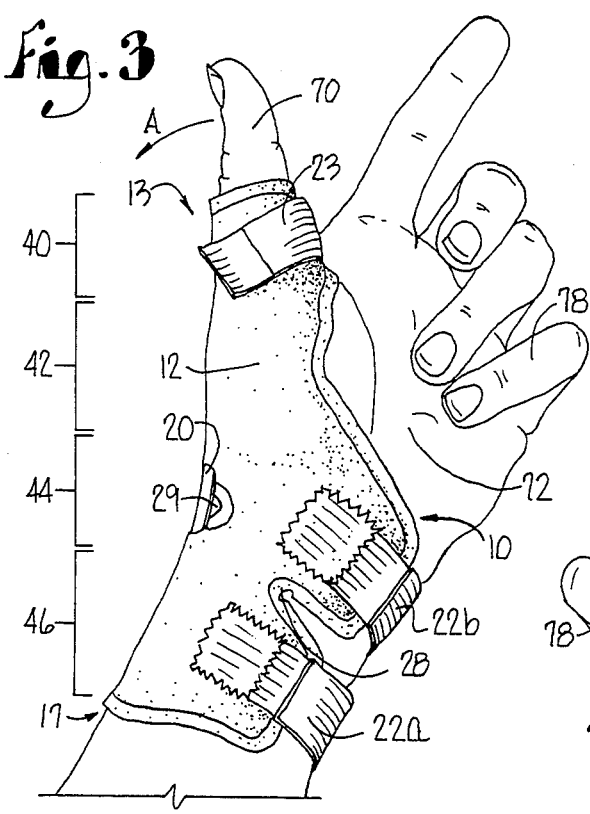
FIG. 3 illustrates the application of the device to the left hand and thumb and shows the unobstructed palm of the user.

Referring now to FIG. 1, an embodiment of the present invention for supporting the thumb of a user (FIGS. 3, 4 and 5) is shown in fragmentary plan view. Thumb brace 10 is shown as it would appear laid out flat, a portion of outer flexible layer 12 being removed to reveal the components sandwiched between outer layer 12 and cushioned base layer 14. Cushioned base layer 14 is composed of a soft sponge-like material such as neoprene which is comfortable to the user and which will not chafe or otherwise irritate the portions of the hand with which it is in contact.

A relatively thin, sheet-like support member 16 overlies base layer 14 and is formed of a thermoplastic material having a molding temperature in the range of greater than approximately 100° F. and less than approximately 180° F. These limitations of the molding temperature are a function of the direct molding feature of the brace 10. This feature permits direct application of the warmed, and thus pliable, support member 16 to the body of the user for direct molding of support member 16 about the thumb or other appendage. In this manner, the specific shape of the particular user becomes embodied in support member 16.

As a result of this method of molding support member 16, it is desirable to utilize a thermoplastic material for the support member 16 which achieves its malleable or moldable state at a temperature range which may be comfortably applied to the skin of the user. Further, it is desirable that the thermoplastic temperature of the support material be above the temperature of the human body so member 16 remains resilient while performing its function. Therefore, a material which has its thermoplastic molding temperature generally in the range of from 100° F. to 180° F. is desired for this application.

Also contained between base cushion layer 14 and outer flexible layer 12 is a means for receiving a splint 20, such means comprising opposed splint pockets 18, 19 aligned along the longitudinal axis of the dorsal surface of the thumb when thumb brace 10 is in place on either the right or the left hand. This positions splint 20 to properly support the thumb in the manner to be described herein. Splint 20 is removeably received within splint pockets 18, 19 in order that splint 20 may be removed during the molding method employed to conform thumb brace 10 to the user. Additionally, splint 20 may be removed from distal splint pocket 18 and proximal splint pocket 19 in order to trim the length of splint 20 to provide greater mobility of the thumb. Alternatively, a user can substitute a more rigid splint material for less flexibility or remove the splint completely to allow maximum flexibility of the thumb.

The outer flexible layer 12 covers base layer 14, support member 16, and splint pockets 18, 19. The layer 12 serves to sandwich the components between the cushion base layer 14 and outer layer 12 and serves to provide a generally smooth uninterrupted outer surface to thumb brace 10 which reduces the chances for snagging the device on objects as well as providing a strong outer layer of protection for the device components. Outer layer 12 is composed of heavy nylon type fabric, in particular 420 nylon denier. The nylon utilized in the invention has a urethane backing which faces base cushion layer 14 and which can be heat bonded to the LYCRA ® surface on the neoprene of cushion base layer 14.

Still referring to FIG. 1, VELCRO ® fastening tabs 22a, 22b and 23 are attached at three positions on thumb brace 10 in order to secure the device. These are employed as shown in FIG. 3. Fastener 22a secures proximal end 17 or wrist segment 46 about the wrist. Midsection 44 is attached around the back of the hand by fastener 22b to provide support of the thenar eminence of the thumb. Fasteners 22a, 22b and 23 provide a rapid and secure method of attaching thumb brace 10 to the hand and allow easy manipulation of the support and fasteners by the single hand of the user available. Fastener 23 secures distal end 13 of thumb brace 10 to the proximal phalange of the thumb to support the joint between the first metacarpal and the proximal phalange. Fastener 23 is a VELCRO ® wool strip and directly attaches to a VELCRO ® hook tab which is sewn to outer layer 12 on the opposite, right side of thumb brace 10 from fastener 23, the stitching being visible at 30 in FIG. 2. Fasteners 22a and 22b wrap around the base of the hand and the wrist and pass through fastener loops 24 and double back upon themselves to allow VELCRO ® hook portion 25 to attach to VELCRO ® wool portion 26 thereby securing thumb brace to the base of the hand and the wrist of the user.

To assist in closely conforming thumb brace 10 to the shape of the hand, a slot is provided at 28 to allow greater contact of thumb brace 10 with the wrist area and to eliminate bunching and puckering of thumb brace 10 about the conjunction of the hand and wrist.

Method of Shaping the Support Member

As previously indicated thumb brace 10 is provided with a moldable support member 16 which permits the user to form the support about his or her own thumb. This feature is of particular utility as it allows the thumb brace 10 to be shaped to the hand of the specific user. By shaping support member 16, brace 10 can be adapted to variations in thumb size as well as to any initial swelling of strained or injured tissue immediately after the injury. As the thumb begins to heal and swelling diminishes, moldable support member 16 can be remolded to provide a closer fit about the thumb and to better guide thumb movement.

Molding of support member 16 is accomplished by heating the thermoplastic material comprising support member 16 until it reaches its pliable or moldable state. Depending upon the plastic selected, this could be a wide range of temperatures. However, as it is desired that the user be able to directly shape support 16 of thumb brace 10 on the hand, the plastic or molding temperature of support 16 should be comfortable to the user when the device is pressed against the hand. Therefore, a plastic having a molding temperature at which the plastic is pliable having an upper range of approximately 180° is desirable.

The other limitation on the molding temperature of the plastic is that it must be sufficiently high so as to remain rigid at the normal temperatures encountered during use. This dictates that a lower end of the moldable temperature range of the plastic utilized in support 16 be greater than approximately 100° F. This produces a temperature range for the moldable or pliable state of the thermoplastic utilized in support 16 of greater than 100° F. and less than approximately 180° F.

Heating of the moldable support is most easily accomplished by the use of a warm liquid, such as hot water, in which the entire thumb brace 10 can be submersed. The thumb brace is immersed in the hot water for a few minutes until support 16 becomes pliable and moldable. After support member 16 has become warm and reaches its moldable state, thumb brace 10 is then applied to the hand of the user. Distal end 13 of thumb brace 10 is applied to the back of the thumb and proximal brace end 17 is applied to the radial side of the wrist. This aligns splint pockets 18, 19 along the dorsal surface of the longitudinal axis of the thumb. Splint 20 has been removed prior to the immersion of thumb brace 10 in hot water.

Once thumb brace 10 is aligned on the hand in the manner described, support member 16 can be molded to the middle and base of the thumb using the opposite hand. Distal wings 32a, 32b of support member 16 are pressed about the side of the thumb sufficiently to permit securing fastener 23 loosely about the thumb. Fasteners 22a, 22b are then also loosely secured. The user then more closely molds the protective support member 16 into a shell about the middle and base of the thumb. As support member 16 is molded to the desired shape, fasteners 22a, 22b and 23 are then firmly secured about the hand to achieve a close fit between thumb brace 10 and the hand.

The shaping of support member 16 results in distal support segment 40 (FIG. 2) being closely formed about the thumb just below the inter phalangeal joint. Neck segment 42 of thumb brace 10 is adjacent to the joint between the proximal phalange and the first metacarpal. Neck 42 is narrowed to provide greater ease of movement and to avoid obstructing the palm of the hand. Mid-section 44 of thumb brace 10 covers the thenar eminence or the base of the palm, and the back of the hand. Support is provided by proximal support wings 36a, 36b of support member 16. Wrist segment 46 of thumb brace 10 covers the wrist area below the base of the hand and serves to brace the wrist while distributing forces applied to the hand and thumb along the wrist and forearm.

When moldable support member 16 has been shaped to the satisfaction of the user, support 16 can be returned to its rigid supportive state by immersing thumb brace in cool water. This cooling lowers the temperature of the plastic of support 16 to a temperature below its moldable state and fixes the shape of support 16 in the shaped conformation. Should the user desire to reshape support 16 or if thumb brace 10 is to be applied to a different user, the molding steps may be repeated upon the same device and a new conformation imparted to support 16.

After thumb brace 10 has been formed to the hand and cooled, splint 20 can then be re-inserted into its position between outer layer 12 and distal splint pocket base layer 52 and proximal splint pocket base layer 54 (FIGS. 1 and 6). Layers 52 and 54 cooperate with overlying layer 12 to form distal splint pocket 18 and proximal splint pocket 19.

Referring to FIG. 6, the construction of thumb brace 10 may be seen in cross-sectional view taken along line 6—6 of FIG. 1. FIG. 6 is presented as an exploded view to indicate the relationship between the components of thumb brace 10. Outer layer 12 is secured to both base layer 14 and distal splint pocket base layer 52 and proximal splint pocket base layer 54. Support member 16 is disposed between outerlayer 12 and base layer 14. The urethane backing 50 on the nylon denier of outer layer 12 is welded to the LYCRA ® layer 56 on neoprene base cushion layer 14. Thermal welding may be employed to heat the two sheets and thereby create a bond between urethane layer 50 and LYCRA ® layer 56 along the margin 57 of the device.

Figure 4:
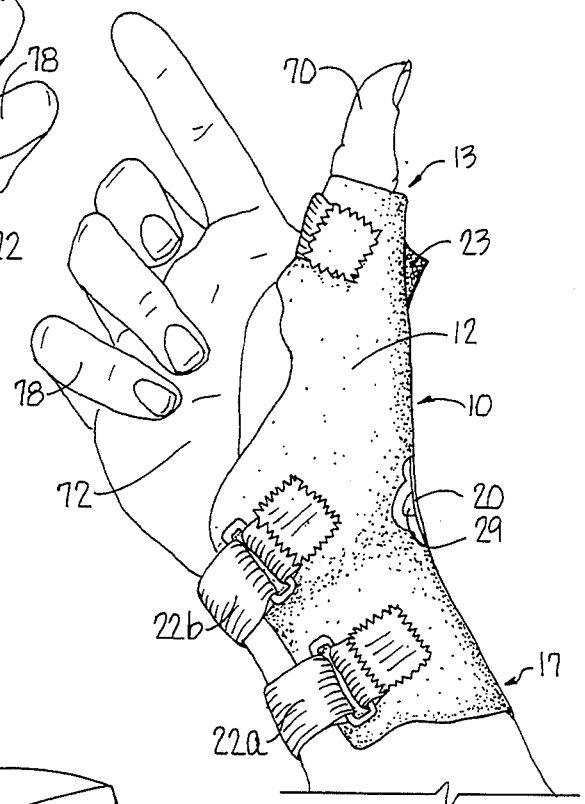
FIG. 4 also shows the device applied to the right hand of a user.

Referring to FIG. 3 and FIG. 4, thumb brace 10 is shown applied to the left and the right hand of a user. Thumb brace 10 provides support for the thumb and wrist and is easy to apply to or remove from either hand. Brace 10 is reusable by the individual. Also, if brace 10 utilized as a piece of equipment in a school sports program, the device is transferrable from user to user as it can be remolded to accommodate each user. This provides a substantial cost savings over devices which only can be used once and then must be discarded. The inventive device provides a number of benefits over the use of elastic bandages or taping of the hand. It will not loosen or come apart under the strain of use. Neither will perspiration nor moisture interfere with the use of the support.

Previously, medical thought adhered to the practice of immobilization of injured limbs to permit proper healing. Current medical treatment, however, has discarded this notion of immobilization in favor of early limited, but structured use of the injured limb, the belief being that the return to activity promotes more rapid and efficient healing and provides more rapid attainment of complete limb mobility. The brace 10 of the present invention provides this type of therapeutic support by guiding a normal range of motion while avoiding unnecessary restriction of hand function.

Referring again to FIG. 3 and FIG. 4, brace 10 is shown in its functional position on both left and right hands. Palm 72 of the hand is completely unobstructed permitting full use of the hand in a substantially normal manner. This lack of obstruction of palm 72 is important in achieving the medically desirable functional use of the hand by permitting use of the hand and thumb in a wide range of tasks.

Support of thumb 70 is provided in several ways. Support member 16 serves to guide opposition or flexion of thumb 70 as it moves across palm 72 to contact finger 78. During this movement, support 16, which is held in place by the entirety of brace 10, directs flexion of the thumb and resists movement to either side of the line of travel of thumb 70 toward finger 78. Support member 16 also serves to restrict excess extension of thumb 70 as distal wings 32a, 32b (FIG. 1) restrict motion of thumb 70 toward the back of the hand.

Splint 20 provides a means for imparting variable resistance to abduction of thumb 70. The movement of thumb 70 back toward the wrist, or abduction, is shown in FIG. 3 by arrow A. The resistance of splint 20 against abduction may be reduced by shortening the length of splint 20. When splint 20 is shortened movement of the thumb along arch A will continue until the ends of splint 20 meet the resistance provided by the closed ends of pockets 18, 19. In this manner shortening splint 20 provides a greater range of abduction motion whereas lengthening splint 20 reduces the range of motion.

To shorten splint 20, it is removed from splint pockets 18, 19, trimmed to a shorter length and then re-inserted. Alternatively, the user can substitute a more or less rigid splint material to change the resistance. In instances where limitation of abduction is not a concern, splint 20 may be eliminated completely.

Figure 5:
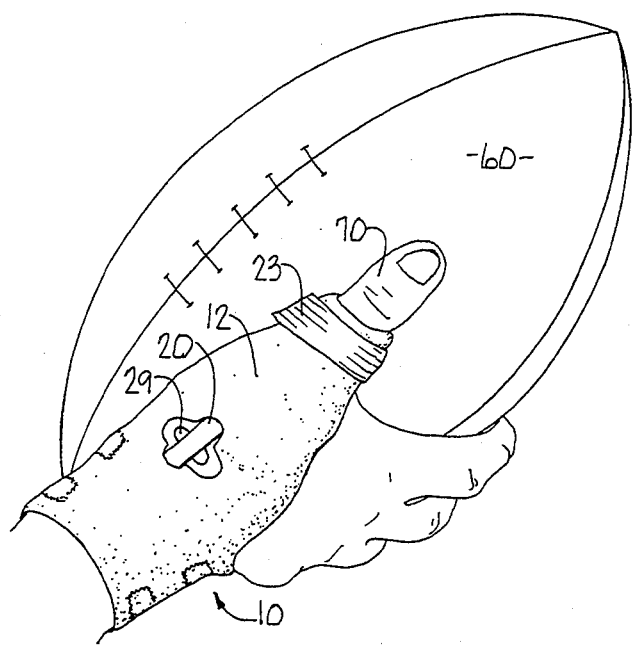
FIG. 5 shows the device applied to the right hand of a user and illustrates the substantially unimpaired ability of the supported thumb to contact and grasp an object.

The slot 28 provides a joint near the junction of the wrist segment 46 and mid-segment 44 to achieve a close fit on the hand. Central opening 29 is also provided to eliminate wrinkling of brace 10 in the area of splint 20. In this manner, a close fit of brace 10 to the hand is achieved which allows a wide range of hand function and yet provides firm, directed support of the hand during activity. As shown in FIG. 5 the device can be utilized to support thumb 70 while allowing the hand to apply sufficient pressure to grip a football 60. This is enabled due to the non-interfering design of brace 10 which provides direction and support to thumb movement without obstructing the palm of the hand or the distal phalange of the thumb.

It is to be understood that while certain forms of this invention have been illustrated and described, it is not limited thereto except insofar as such limitations are included in the following claims and allowable equivalents thereof.

Having thus described the invention, what is claimed as new and desired to be secured by Letters Patent is as follows:

1. An apparatus worn on a hand for supporting a digit thereof, said apparatus including a digit-supporting portion and a wrist segment and comprising:

a base cushion layer, a outer flexible layer overlying said base layer, a relatively thin, sheet-like support member retained between said layers and moldable to conform to the shape of said digit and guide movement thereof through a normal range of motion, said member having a shape which, when the apparatus is in a functional position on a hand of a wearer, leaves the pal of the hand substantially unobstructed, and said member in said functional position extending inwardly within said digit-supporting portion toward and terminating in spaced relationship to a wrist segment of the apparatus so that the mobility of the wrist of a wearer is not impaired, and means for fastening the apparatus to the hand and the selected digit of a wearer to hold the apparatus in said functional position on the back of the hand and digit, whereby to provide support thereto without immobilizing the hand or digit.

2. The apparatus as claimed in claim 1, wherein the supported digit is the thumb of a wearer, said member in said functional position extending inwardly and laterally into embracing relationship with exclusively the first metacarpal and terminating therebeyond, whereby said palm of the hand is substantially unobstructed.

3. The apparatus as claimed in claim 1, wherein the supported digit is the thumb of a wearer, said member having a distal portion for disposition at the dorsal region of the thumb and a pair of opposed, proximal wings extending inwardly and laterally into embracing relationship with exclusively the first metacarpal and terminating therebeyond, whereby said palm of the hand is substantially unobstructed.

4. The apparatus as claimed in claim 3, wherein said distal portion of the member is provided with a pair of opposed, distal wings which, in said functional position of the member, are formed about the thumb adjacent the interphalangeal joint.

5. The apparatus as claimed in claim 1, further comprising a splint of predetermined length, and wherein said outerlayer is provided with means presenting a pair of opposed, dorsal, proximal and distal pockets for slidably receiving said splint and cooperating therewith to provide a desired resistance to abduction determined by the length of the splint.

6. The apparatus as claimed in claim 1, wherein said base cushion layer comprises neoprene.

7. The apparatus as claimed in claim 1, wherein said support member comprises a thermoplastic material moldable in a temperature range of greater than approximately 100° F. and less than approximately 180° F.

8. The apparatus as claimed in claim 1, wherein said outer layer comprises nylon.

9. The apparatus as claimed in claim 1, further comprising means fusing said outer layer with said base layer along a margin thereof to join said layers together.

10. The apparatus as claimed in claim 1, wherein said means for fastening comprises straps for securing the apparatus to the hand.

11. The apparatus as claimed in claim 1, wherein said support member has a distal portion for disposition at the dorsal region of the digit, and a pair of opposed, proximal wings for supporting the hand adjacent the base of the digit.

12. The apparatus as claimed in claim 1, further comprising a splint of predetermined length, and wherein said outer layer is provided with means for slidably receiving said splint for movement of the splint in said receiving means to a position providing resistance against abduction.

13. The apparatus as claimed in claim 2, wherein said splint has a length selected to impart a desired resistance to abduction.

* * * * *

UNITED STATES PATENT AND TRADEMARK OFFICE
CERTIFICATE OF CORRECTION

PATENT NO.   : 5,356,371
DATED        : October 18, 1994
INVENTOR(S)  : Craig J. Hubbard It is certified that error appears in the above-indentified patent and that said Letters Patent is hereby corrected as shown below:

Claim 1, column 7, line 15, after the first occurrence of the word "the" delete "pal" and insert --palm--.

Claim 1, column 7, line 19, after "to" delete "a" and insert --said--.

Claim 5, column 8, line 8, after "said" delete "outerlayer" and insert --outer layer--.

Claim 13, column 8, line 38, after "claim" delete "2" and insert --12--.

Signed and Sealed this

Twentieth Day of December, 1994

Attest:

BRUCE LEHMAN

Attesting Officer    Commissioner of Patents and Trademarks